US00PP31755P2

(12) United States Plant Patent
Hansen

(10) Patent No.: US PP31,755 P2
(45) Date of Patent: May 12, 2020

(54) ***ACHILLEA* PLANT NAMED 'SASSY SUMMER TAFFY'**

(50) Latin Name: ***Achillea* hybrid**
Varietal Denomination: Sassy Summer Taffy

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,802

(22) Filed: Jan. 14, 2019

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 6/14
See application file for complete search history.

*Primary Examiner* — Anne Marie Grunberg

(57) ABSTRACT

The new and distinct Yarrow, *Achillea* plant named 'Sassy Summer Taffy', with narrow, moderate green, highly-dissected, fern-like foliage; tall, stiff, heavily branched peduncles with purplish-red inflorescences, beginning in mid-June and continuing for about six weeks. The new plant is useful for landscaping, as a specimen or en masse and as a cut flower.

1 Drawing Sheet

Botanical designation: *Achillea* hybrid.
Cultivar denomination: 'Sassy Summer Taffy'.

STATEMENT REGARDING PRIOR DISCLOSURES UNDER 37 CFR 1.77(B)(6)

The first public disclosure of the claimed plant, in the form of a sale, was made by Walters Gardens, Inc. on Jul. 9, 2018. Prior to that, on Feb. 1, 2018 the claimed plant was displayed as a photograph with a brief description on a website operated by Walters Gardens, Inc., who obtained the plant and all information relating thereto, from the inventor. No plants of *Achillea* 'Sassy Summer Taffy' have been sold, in this country or anywhere in the world, nor has any disclosure of the new plant been made, more than one year prior the filing date of this application, and such sale or disclosure within one year was either derived directly or indirectly from the inventor.

BACKGROUND OF THE PLANT

The present invention relates to the new and distinct yarrow herein also referred to as *Achillea* 'Sassy Summer Taffy', by the cultivar name, 'Sassy Summer Taffy', or as the new plant. The new plant was selected by the inventor as a single seedling resulting from a cross in an isolation block between a proprietary unreleased plant identified with the breeder code 13-5-13 (not patented) crossed with siblings of 13-5-13 (not patented) in research facility of a wholesale perennial grower based in Zeeland, Mich., USA. The seeds from this cross were collected on Sep. 23, 2014. The single seedling was then isolated and compared in subsequent years to other Yarrow and subsequently found to be different from all cultivars known to the discoverer and eventually given the breeder code 14-28-1.

Asexual propagation at the same nursery in Zeeland, Mich., USA initially by division and then by cuttings has shown 'Sassy Summer Taffy' to be stable and reproduce true to type in successive generations.

SUMMARY OF THE PLANT

*Achillea* 'Sassy Summer Taffy' has not been observed in all possible environmental conditions. The phenotype may vary slightly with changes in environments such as light intensity, fertility, water availability, etc. without, however any variation in genotype.

*Achillea* 'Sassy Summer Taffy' is distinct from all cultivars known to the inventor in the following traits:

1. Narrow, moderate green, fern-like foliage with tall height and densely upright habit.
2. Numerous large panicles of purplish-red inflorescences that mature to light peachy-pink.
3. Heavily-branched peduncles with center main cluster to about 11.0 cm across.
4. Sturdy stems withstand wind and rain.
5. Long flowering period beginning early to mid-June and continuing for about six weeks.

Plants of *Achillea* 'Sassy Summer Taffy' are most similar to: 'Sassy Summer Sangria' U.S. Plant patent application Ser. No. 16/350,529, 'Strawberry Seduction' U.S. Plant Pat. No. 18,401, 'Saucy Seduction' U.S. Plant Pat. No. 20,782, 'Red Velvet' (not patented) and 'Red Beauty' (not patented). 'Sassy Summer Sangria' has more silvery lanulose foliage with deeper incisions and the flowers are dark reddish. 'Strawberry Seduction' is shorter and more open in habit, has more open flower stems, the flower stems have less branching and the flowers are a different color. 'Saucy Seduction' is shorter in habit, has fewer flower stems, the flowers are a different color and do not change colors as significantly as the new plant. 'Red Velvet' is taller and more open in habit, and the flower color is more reddish. 'Red Beauty' has more silvery and less dissected foliage, the habit is slightly shorter, the umbels are not as wide and the flower color is different.

BRIEF DESCRIPTION OF THE DRAWINGS

The color drawings illustrate the overall characteristics of *Achillea* 'Sassy Summer Taffy' as a three-year-old plant in a full-sun trial garden in Zeeland, Mich. The colors are as true as reasonably possible given the technology available. The color values may vary slightly depending on light intensity and quality.

DETAILED BOTANICAL DESCRIPTION

Figure 1:
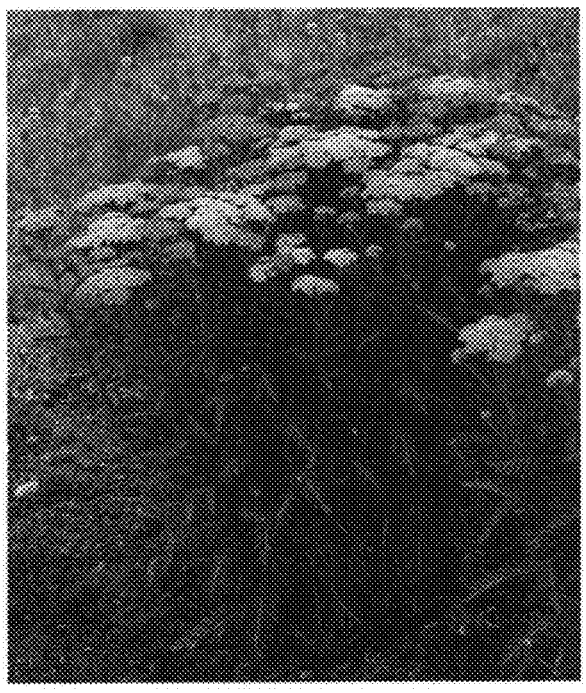
FIG. 1 shows the new plant in a trial facility.
Figure 2:
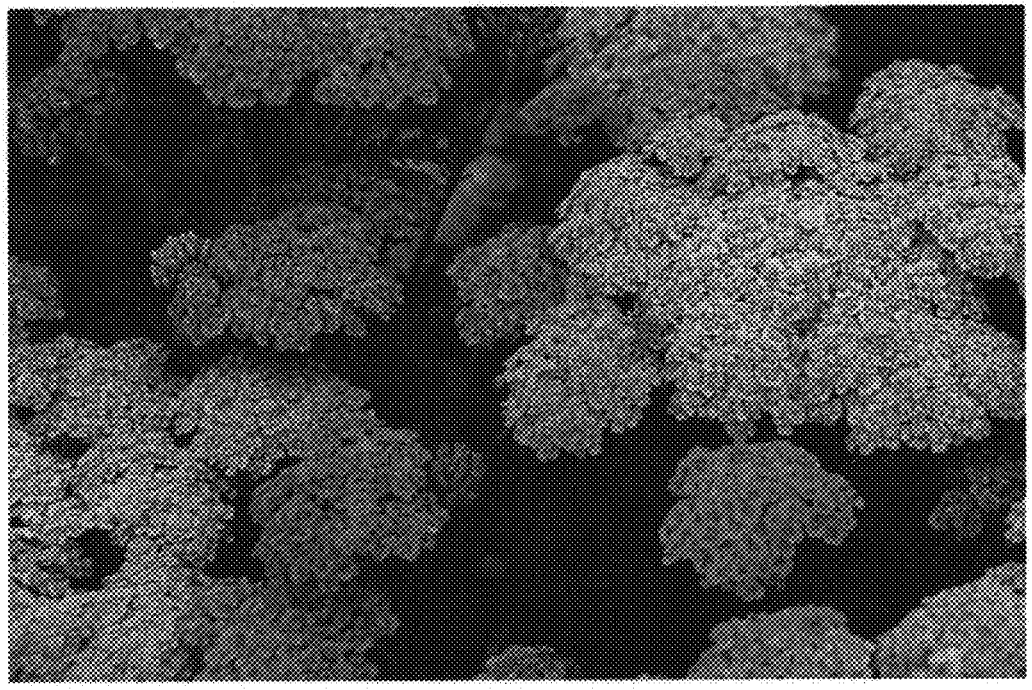
FIG. 2 shows a close-up of the flowers of the new plant.

The following description is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent 13-5-13 which is a hybrid between *Achillea millefolium* 'Strawberry Seduction' U.S. Plant Pat. No. 18,401 and a proprietary selection *A. siberica* (not patented); male or pollen parent is a sibling to 13-5-13;

Asexual propagation: Shoot tip cuttings, about 10 to 14 days to initiate roots; time to finish as # 1 field grown size about 9 months;

Plant habit: Dense axillary branches; upright, heavily-branched, herbaceous, winter-hardy, perennial mound; up to 76.0 cm tall and 78.0 cm wide; average about 72.0 cm tall and about 73.0 cm across;

Leaves: Alternate; glabrous; pinnatisect with lobules deeply incised to midrib; lanceolate; acute apex; base attenuate; caudate sessile, petiolate proximal; sparsely puberulent abaxial and adaxial and sparsely lanulose abaxial midrib; up to 34.0 cm long and 4.0 cm wide, with individual lobes to 14.0 mm wide and 3.1 cm long, average about 23.0 cm long and 4.0 cm wide; fragrance of faint herbal;

Leaf color: Young expanding leaves adaxial nearest RHS 139A, abaxial nearest RHS 137A; mature leaves adaxial nearest RHS 139A with tinting concentrated toward base of lobules of nearest RHS 181A, abaxial nearest RHS 137A;

Veins: Pinnate; only abaxial midrib obvious;

Midrib color: Adaxial nearest RHS 145D with tinting to solid nearest RHS 181A in high light, abaxial lighter than RHS 146D;

Petiole: Channeled; lanulose; to 10.0 cm long and 3.5 mm wide at base; color nearest RHS 146D;

Stems: Upright; cylindrical; lanulose to tomentulose; to about 50 per plant, average 42 per plant; to about 72.0 cm long and 6.5 mm diameter at base; color mature stems nearest RHS 146C with tinting of nearest RHS 178B, young stems between RHS 146D and RHS 145A;

Nodes: About 17 nodes below flower branches; average internode length 2.5 cm below flowers; color same as surrounding stem;

Inflorescence: Radiate; composite consisting of about five ray and about twelve disk florets; on heavily branched terminal stems; individual inflorescence about 4.5 mm diameter, about 5.0 mm tall from bottom of involucral bracts to top of exserted stigmas; disk about 3.0 mm across; attitude mostly upright; producing branched stems with about 400 inflorescences per stem; single branched umbel to about 11.0 cm across;

Receptacle: About 3.0 mm tall; color nearest RHS 148C;

Inflorescence fragrance: Not detected;

Phyllaries: About ten in two whorls; lanceolate; acute apex; truncate base; margin entire; outer or lower set about 2.0 mm long and 1.0 mm across, inner set about 3.0 mm long and 1.0 mm across; glabrous adaxial, pubescent abaxial; tightly adpressed against ray petals;

Phyllary color: Lower set between RHS 147B and RHS 147C adaxial and abaxial, upper set nearest RHS 147B adaxial and abaxial;

Flowering period: Late June, for about 4 weeks;

Flower longevity: 4 to 6 days;

Inflorescence buds: With ray florets still erect 5.0 mm tall and 2.5 mm across; ovoid;

Inflorescence bud color: Ray florets while still upright exposed petal color nearest RHS 63A distally and nearest RHS 62D just above phyllaries; phyllaries color nearest RHS 147C;

Peduncle: Cylindrical; slightly lanulose to tomentulose; strong; upright attitude; heavily branched; up to 6.5 mm diameter at base, average 4.5 mm diameter; and 72.0 cm long, flowering in upper 7.0 cm; branches to about 17.0 cm long and 4.0 mm diameter at base;

Peduncle color: Between RHS 146C and RHS 146D;

Ray florets: Imperfect; staminate; typically about five per inflorescence; containing only gynoecium with style about 2.5 mm long and split stigma;

Ray floret ligule: Rounded with basal claw; apex rounded to slightly emarginate, margin entire; base claw, attenuate; opening to about a 90 ° angle; glabrous adaxial and adaxial; about 4.0 mm long and about 5.0 mm wide; basal claw about 1.5 mm long and about 0.5 mm across;

Young ray floret ligule color when first flat: Adaxial between RHS 63A and RHS 63B, abaxial nearest RHS 181D;

Mature ray floret ligule color: Adaxial nearest RHS 186D transitioning to a blend between nearest RHS 186D and RHS 159D; abaxial nearest RHS 159D;

Style: Cylindrical; about 2.0 mm long and 0.2 mm diameter; exserted; color nearest RHS 18D;

Stigma: Bifid; about 1.5 mm long and 0.2 mm diameter; color nearest RHS 18D;

Disk florets: About twelve per capitulum; tubular; glabrous; consisting of tepals, staminal tube and pistil; size about 3.5 mm long by 1.0 mm wide at apex;

Tepals: Five; 2.5 mm long and 0.7 mm wide, fused in the basal 2.0 mm, acute apex;

Tepal color: Nearest RHS 161D;

Staminal tube: Made up of five adnate stamens; about 2.0 mm long;

Filaments: Cylindrical; about 0.7 mm long and 0.1 mm diameter; color nearest RHS NN155A;

Anther: About 1.0 mm long; color nearest RHS 17B;

Pollen: Fine, round, closest to RHS 17B;

Style: Bifid; cylindrical; exserted; about 2.0 mm long and 0.2 mm diameter; color nearest RHS 18B;

Stigma: Bifid; reflexing as it matures; about 1.5 mm long; color nearest RHS 18D;

Seed: Flattened deltoid; acute apex and truncate base; surface glabrous; about 2.0 mm long and 0.7 mm across base;

Seed color: Between RHS 165A and RHS 165B in center and RHS 161D around edges;

*Achillea* 'Sassy Summer Taffy' is tolerant of winter temperatures as low as −35° C. and summer temperatures as high as 38° C. It is not known to be tolerant of diseases and pest that are common to other *Achillea* cultivars.

I claim:

1. The new and distinct cultivar of *Achillea* plant named 'Sassy Summer Taffy' as described and illustrated.

* * * * *